United States Patent
Risse

(10) Patent No.: US 7,694,365 B2
(45) Date of Patent: Apr. 13, 2010

(54) PILLOW FOR FIXING OF SHOULDERS OF PATIENTS IN MAGNETIC RESONANCE ACQUISITIONS

(75) Inventor: Wolfgang Risse, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/035,494

(22) Filed: Feb. 22, 2008

(65) Prior Publication Data

US 2008/0201852 A1    Aug. 28, 2008

(30) Foreign Application Priority Data

Feb. 22, 2007   (DE) .................. 10 2007 008 741

(51) Int. Cl.
*A61G 7/05* (2006.01)
*A61G 13/10* (2006.01)
(52) U.S. Cl. ............................. 5/601; 5/621; 128/845
(58) Field of Classification Search ............ 5/601, 5/621, 622, 630, 636, 652, 655.9, 953; 378/209; 128/845, 846
See application file for complete search history.

(56) References Cited

U.S. PATENT DOCUMENTS

| | | | | |
|---|---|---|---|---|
| 3,848,281 A * | 11/1974 | Mathews | ................ | 5/636 |
| 5,997,572 A * | 12/1999 | Arnold et al. | ................ | 607/104 |
| 6,228,107 B1 * | 5/2001 | Arnold et al. | ................ | 607/104 |
| 6,241,755 B1 * | 6/2001 | Arnold et al. | ................ | 607/104 |
| 6,309,408 B1 * | 10/2001 | Arnold et al. | ................ | 607/104 |
| 6,550,085 B2 * | 4/2003 | Roux | ................ | 5/654 |
| 6,666,879 B2 * | 12/2003 | Arnold et al. | ................ | 607/104 |
| 6,684,430 B2 * | 2/2004 | Roux | ................ | 5/654 |
| 7,000,335 B2 * | 2/2006 | Swigart et al. | ................ | 36/29 |
| 7,013,171 B2 * | 3/2006 | Rhodes | ................ | 600/407 |
| 7,031,763 B1 | 4/2006 | Zhang | ................ | 600/422 |
| 7,048,703 B2 * | 5/2006 | Riach | ................ | 602/13 |
| 7,244,268 B2 * | 7/2007 | Arnold et al. | ................ | 607/104 |
| 7,426,930 B1 * | 9/2008 | Bailey et al. | ................ | 128/845 |
| 7,434,339 B2 * | 10/2008 | Swigart et al. | ................ | 36/29 |
| 2001/0012957 A1 * | 8/2001 | Arnold et al. | ................ | 607/104 |
| 2002/0013967 A1 * | 2/2002 | Roux | ................ | 5/654 |
| 2003/0131417 A1 * | 7/2003 | Roux | ................ | 5/654 |
| 2005/0011085 A1 * | 1/2005 | Swigart et al. | ................ | 36/31 |
| 2008/0201852 A1 * | 8/2008 | Risse | ................ | 5/646 |

OTHER PUBLICATIONS

Printout of GE Healthcare Web Page for 3.0T High Density Arrays (Feb. 2006).

* cited by examiner

*Primary Examiner*—Robert G Santos
(74) *Attorney, Agent, or Firm*—Schiff Hardin LLP

(57) ABSTRACT

A pillow, for supporting and fixing the shoulders of an examination subject in the respective housings of different shoulder coils in a magnetic resonance apparatus, snugly fills the inner area of the shoulder coil with at least three, and preferably four lobes with the lobes not laterally overlapping one another.

12 Claims, 2 Drawing Sheets

PILLOW FOR FIXING OF SHOULDERS OF PATIENTS IN MAGNETIC RESONANCE ACQUISITIONS

BACKGROUND OF THE INVENTION

1. Field of the Invention

The present invention concerns a pillow for supporting and fixing the shoulders of an examination subject in the housing of a shoulder coil in a magnetic resonance apparatus.

2. Description of the Prior Art

In magnetic resonance data acquisitions, the shoulders of the subject must be supported and fixed comfortably. Furthermore it is important for a specific distance to be maintained between the inner surface of a shoulder coil and the shoulders, in order to minimize unwanted signals that originate from the subcutaneous fat layer of the shoulders. There have previously been no standardized, commercially produced solutions in order to satisfy the above conditions. Makeshift solutions such as hand towels or foam padding that were not tailored to the shape of the inner surface of the shoulder coil have been used.

The problem is thus that the aforementioned makeshift solutions do not represent uniform, reproducible devices in order to fix the shoulders at a fixed, optimal distance from the inner surface of the shoulder coil.

SUMMARY OF THE INVENTION

An object of the present invention is to provide a device with which the shoulders of a patient can be comfortably supported, fixed and held at a fixed distance from the inner surface of the shoulder coil during a magnetic resonance acquisition.

The above object is achieved in accordance with the invention by a pillow for supporting and fixing the shoulders in the housings of shoulder coils in magnetic resonance apparatuses, that snugly fills the inner area of the shoulder coil with at least three, and preferably four lobes, with and the lobes not laterally overlapping each other in the housing.

The present invention is advantageous for a number of reasons. The basis of the invention is a pillow that enables the comfortable support of the shoulders of patients at a fixed distance from the inner side of the shoulder coil of a magnetic resonance system. The pillow has a unit size that fits all shoulder coil sizes and shoulder sizes. The pillow is thus universally usable and can be industrially produced in a large quantity and in a uniform shape size. Furthermore, the pillow exhibits a good filling factor due to its structure composed of a number of lobes.

DESCRIPTION OF THE PREFERRED EMBODIMENTS

Figure 1:
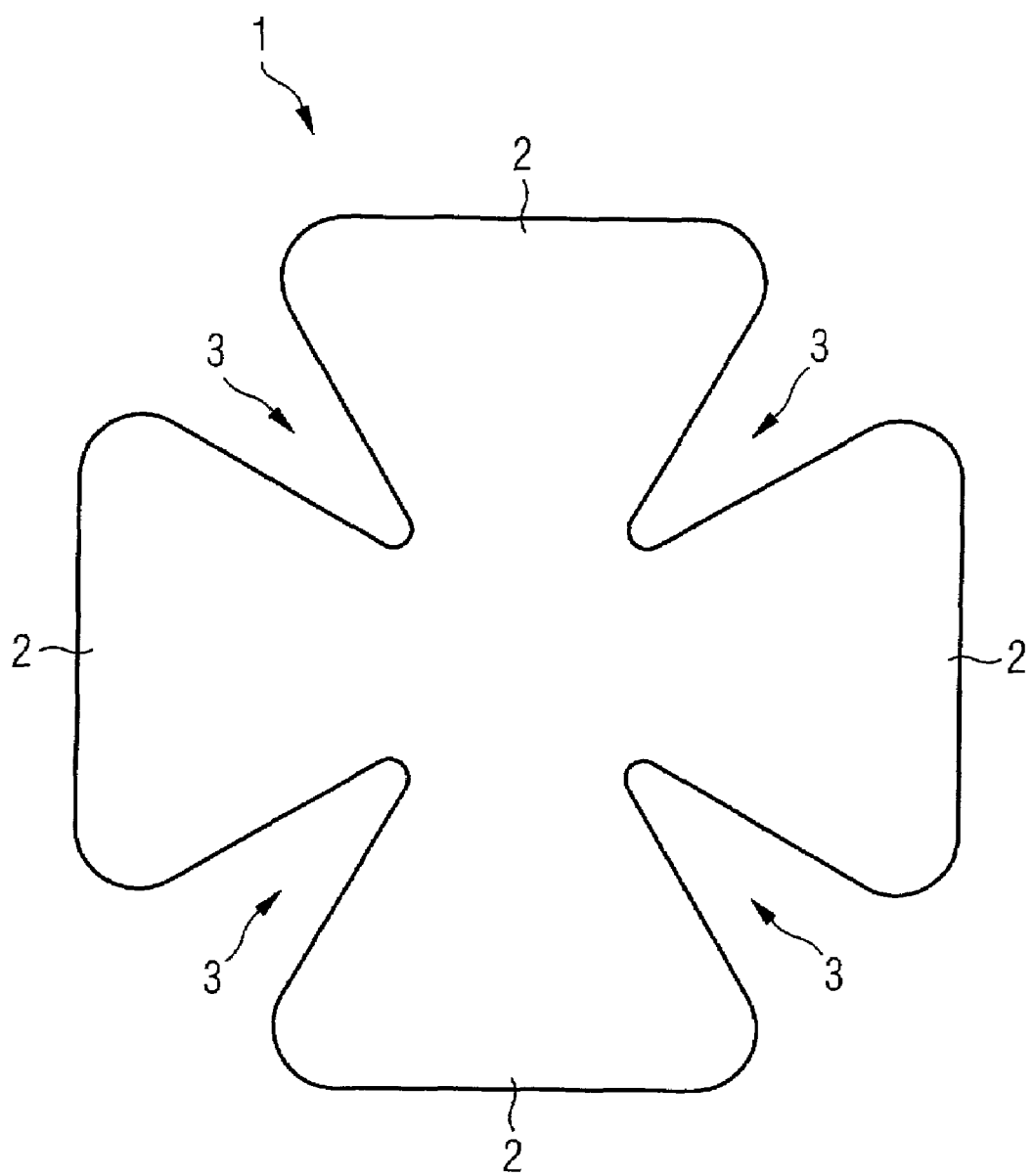
FIG. 1 is a schematic depiction of a pillow in accordance with the invention.

FIG. 1 shows an exemplary embodiment of the present invention, namely a pillow 1 for supporting and fixing of the shoulders of a subject in housings of shoulder coils in magnetic resonance apparatuses.

Figure 2A:
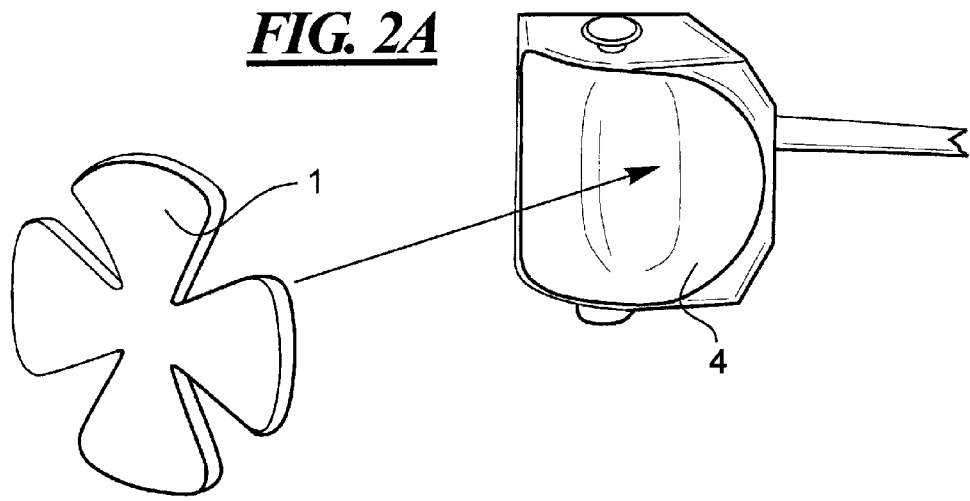
FIG. 2A schematically illustrates a pillow in accordance with the invention before insertion into a magnetic resonance shoulder coil.
Figure 2B:
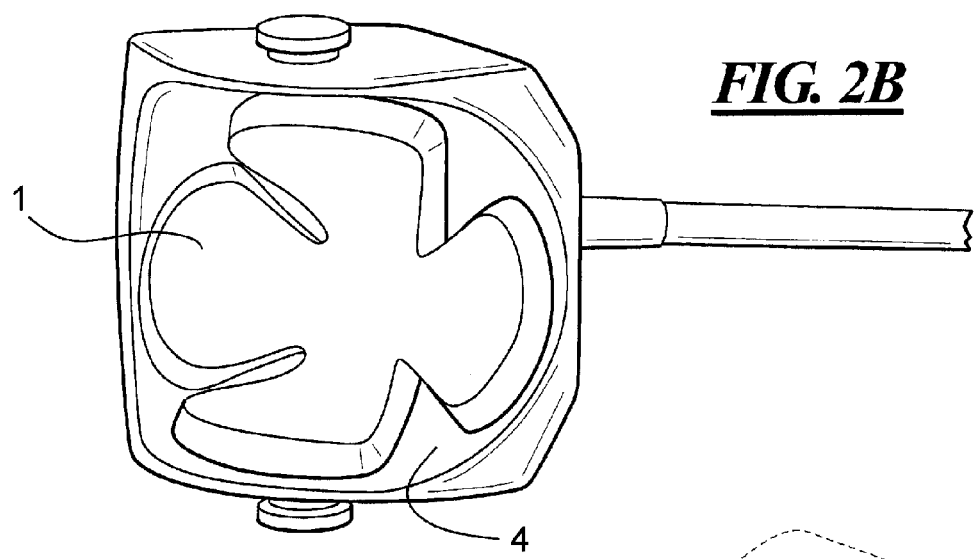
FIG. 2B shows the pillow in accordance with the present invention fitted into a magnetic resonance shoulder coil.
Figure 2C:
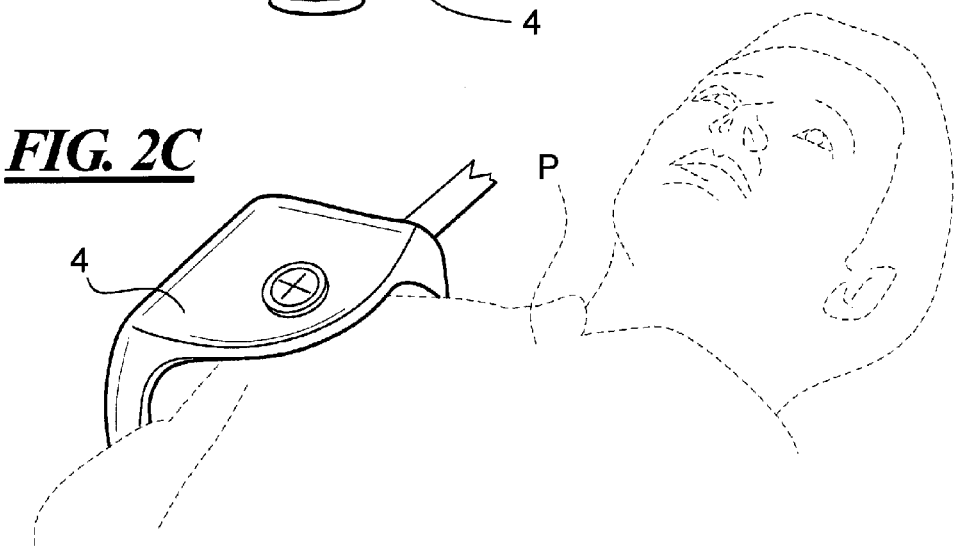
FIG. 2C shows the shoulder coil with the pillow fitted therein in place on the shoulder of a patient in a magnetic resonance apparatus.

As shown in FIGS. 2A and 2B, a shoulder coil 4 for which the inventive pillow 1 is used, has a housing in which, for example, four coil elements are contained that are designed as flat copper conductive traces in the form of ovals. Magnetic resonance signals can be detected therewith with high spatial resolution. The housing ensures that a minimum distance is maintained between the (for example four) elements of the shoulder coil 4 and the shoulder surface, which prevents an unwanted heating of the shoulder to be examined. The shoulder coil 4 is fastened in a fixed manner on the patient table (bed) that is slid into the opening of the magnetic resonance system for the examination (data acquisition). Depending on whether the right or left shoulder of the patient P (shown in FIG. 2C) is to be examined, there are various positions in which the shoulder coil can be placed on a base plate that in turn rests on the patient table. In order to acquire an optimally good signal from the shoulder regions to be examined and to comfortably support the shoulder, a spacer can additionally be provided between the inner surface of the shoulder coil and the shoulder of the patient. The pillow 1 is designed to serve such a spacer.

The pillow 1 is provided with at least three, and preferably four, lobes 2 that snugly fill the inner area of the shoulder coil. The lobes 2 do not laterally overlap after the pillow 1 is placed in the shoulder coil.

In the version of the pillow 1 with four lobes 2, these are arranged in the form of a four-leaf clover. V-shaped openings 3 are respectively punched out between the lobes 2. These openings 3 ensure that the lobes 2 of the pillow 1 do not laterally overlap after the placement of the pillow 1 in the shoulder coil.

The pillow 1 can exhibit a thickness of 5 mm through 25 mm and advantageously 12 mm in order to provide the desired large distance between the inner surface of the shoulder coil and the shoulder that signals from the subcutaneous fat layer of the shoulder are largely suppressed. These signals are undesirable because they overlap the relevant signals from fluids or cartilage of the shoulder and adulterate the acquired signals. A value must be found for the thickness of the pillow 1 for which the signals from the fat layer are sufficiently small but the desired signals (which likewise decrease given increasing distance of the shoulder from the shoulder coil) are still large enough to yield a sufficiently strong signal at a given signal/noise ratio.

Furthermore, it is important that the material for the pillow 1 not be image-producing (i.e., it should not make a contribution to the result MR image). The pillow 1 should be invisible or generate no artifacts in the magnetic resonance images. The pillow 1 must additionally be formed of material that is biocompatible, thus does not aggravate or harm the patient.

The pillow 1 can be formed of a number of elastic materials. Foams (such as, for example, foamed material) can advantageously be used. A compromise between deformability and rigidity of the pillow 1 must be found in order to satisfy the concurrent requirements of comfortable support of the shoulder and spacing of the shoulder from the shoulder coil at an approximately fixed value.

The foamed pillow 1 can be covered by a lacquer layer or a film that protects the pillow 1 against abrasion and makes the cleaning of the pillow 1 easier.

The pillow 1 must be formed as a single part in order to make the manufacturing process easier and to achieve a good matching shape without projecting edges in the inner area of the shoulder coil.

Furthermore, the pillow 1 has a unit size that fits both in small shoulder coils with, for example, a 165 mm opening and in large shoulder coils with, for example, a 200 mm opening. Small shoulder coils are suitable for the majority of patients; large shoulder coils must only be used for very muscular or overweight patients.

The pillow 1 can be loosely inserted between the inner side of the shoulder coil 4 and the shoulder of the patient P. It is attached neither to the shoulder coil nor to the shoulder. The slight pressure with which the shoulder is placed in the shoulder coil is sufficient to hold the pillow 1 in position.

Although modifications and changes may be suggested by those skilled in the art, it is the intention of the inventor to embody within the patent warranted hereon all changes and modifications as reasonably and properly come within the scope of his contribution to the art.

I claim as my invention:

1. A support structure that supports a shoulder of an examination subject in a magnetic resonance apparatus, said support structure comprising a magnetic resonance shoulder coil selected, as a selected shoulder coil, from among a plurality of differently sized magnetic resonance shoulder coils, and a pillow having a pillow body formed of material that comfortably supports human anatomy and that does not make a contribution to a magnetic resonance image, said pillow body comprising at least four outwardly extending, spaced-apart lobes having respective sizes and shapes relative to each other that allow said pillow body to be differently configured to respectively snugly fill an inner area in each of said plurality of differently sized magnetic resonance shoulder coils to give said pillow body, in each of said differently sized magnetic resonance shoulder coils, a configuration that supports a shoulder of a patient being examined with the selected shoulder coil in said magnetic resonance apparatus, said sizes and shapes of said lobes causing said lobes to not laterally overlap one another when said pillow body is configured and placed in each of said respectively different sized shoulder coils.

2. A support structure as claimed in claim 1 wherein said pillow body comprises four of said lobes.

3. A support structure as claimed in claim 2 wherein said four lobes of said pillow body are arranged in a four-leaf clover configuration, with a v-shaped opening between each pair of adjacent lobes.

4. A support structure as claimed in claim 1 wherein said pillow body has a thickness that produces a distance between said inner surface and the shoulder of the patient that substantially suppresses magnetic resonance signals originating from a subcutaneous fat layer in the shoulder.

5. A support structure as claimed in claim 4 wherein said pillow body has a thickness in a range between 5 mm and 25 mm.

6. A support structure as claimed in claim 5 wherein said pillow body has a thickness of 12 mm.

7. A support structure as claimed in claim 1 wherein said pillow body is comprised of biocompatible material.

8. A support structure as claimed in claim 1 wherein said pillow body is comprised of elastic foam.

9. A support structure as claimed in claim 8 wherein said pillow body comprises an exterior cover over said elastic foam selected from the group consisting of a lacquer layer and a film.

10. A support structure as claimed in claim 1 wherein said pillow body is formed as a single, unitary body.

11. A support structure as claimed in claim 1 wherein said pillow body has a body size configured to fit within each of a shoulder coil having a 165 mm opening and a shoulder coil having a 200 mm opening, without said lobes overlapping one another in either housing.

12. A support structure as claimed in claim 1 wherein said pillow body is configured to be non-fixedly inserted between an inner surface of the shoulder coil and the shoulder of the patient.

* * * * *